(12) United States Patent  
Vu (10) Patent No.: US 6,685,628 B2
(45) Date of Patent: Feb. 3, 2004

(54) ENDOSCOPIC BALLOON FOR SPILL-PROOF LAPAROSCOPIC OVARIAN CYSTECTOMY

(76) Inventor: Dinh Q. Vu, 1520 Sand Hill Rd. #208, Palo Alto, CA (US) 94304

( * ) Notice: Subject to any disclaimer, the term of this patent is extended or adjusted under 35 U.S.C. 154(b) by 54 days.

(21) Appl. No.: 10/147,261

(22) Filed: May 15, 2002

(65) Prior Publication Data

US 2003/0216611 A1 Nov. 20, 2003

(51) Int. Cl.7 .............................................. A61F 13/00
(52) U.S. Cl. .................. 600/37; 600/207; 606/114; 606/127
(58) Field of Search .................. 600/37, 204, 207; 606/114, 127

(56) References Cited

U.S. PATENT DOCUMENTS

| | | | |
|---|---|---|---|
| 5,215,521 A | | 6/1993 | Cochran et al. |
| 5,279,539 A | | 1/1994 | Bohan et al. |
| 5,337,754 A | * | 8/1994 | Heaven et al. .............. 600/562 |
| 5,341,815 A | * | 8/1994 | Cofone et al. .............. 600/562 |
| 5,352,184 A | * | 10/1994 | Goldberg et al. ............. 600/37 |
| 5,486,182 A | * | 1/1996 | Nakao et al. ................ 606/114 |
| 5,522,790 A | | 6/1996 | Moll et al. |
| 6,045,566 A | | 4/2000 | Pagedas |
| 6,059,793 A | | 5/2000 | Pagedas |
| 6,270,505 B1 | | 8/2001 | Yoshida et al. |

* cited by examiner

Primary Examiner—John P. Lacyk
(74) Attorney, Agent, or Firm—Knobbe, Martens, Olson & Bear, LLP (57) ABSTRACT

An endoscopic balloon device and method of using in a laparoscopic surgical procedure such as a cystectomy is disclosed. An intact organ such as an ovary is encapsulated with the endoscopic balloon while the organ remains attached to the body. By inserting instruments into the bag, a surgical procedure is then performed within the bag, for example, a cyst may be removed from an ovary. After cyst removal, the bag is irrigated to remove leakage before withdrawal of the cyst within the bag.

31 Claims, 11 Drawing Sheets

ENDOSCOPIC BALLOON FOR SPILL-PROOF LAPAROSCOPIC OVARIAN CYSTECTOMY

BACKGROUND OF THE INVENTION

1. Field of the Invention

The invention relates in one embodiment to a method of performing an ovarian cystectomy by laparoscopy using a spill-proof endoscopic device. A spill-proof endoscopic device is also disclosed.

2. Description of the Related Art

Within the context of one embodiment of the present invention, ovarian cystectomy refers to the removal of a cyst from an ovary. Laparotomy refers to the traditional method of opening up the abdomen by making a large incision, typically about 12–14 cm in length. Oophorectomy is defined as the removal of the entire ovary. Laparoscopy is a method of performing intra-abdominal surgery via very small incisions, often 1 cm or less in length. Laparoscopic ovarian cystectomy is the removal of a cyst from the ovary using the technique of laparoscopy.

Ovarian cystectomy is a commonly performed procedure in gynecology. An attendant risk to this procedure, especially if done via laparoscopy, is the accidental leakage of the cyst content into the peritoneal cavity, which occurs most often during the separation of the cyst from the ovary. This can worsen the prognosis if the cyst turns out to be malignant or can lead to peritonitis if the cyst is a dermoid or mucinous cyst. Because of this hazard, ovarian cystectomy by laparoscopy requires more skill, time, and effort than that done via laparotomy if the cyst is to be removed without spillage. Consequently, many surgeons will opt to go directly to a laparotomy or perform a laparoscopic oophorectomy (which has a much lower risk of cyst leakage because the cyst is not separated from the ovary) instead of a laparoscopic cystectomy if he or she is uncertain about the nature of the cyst.

In addition, there is often no way to know in advance if the cyst is malignant, dermoid, mucinous, or otherwise. The physician must rely upon a combination of imprecise diagnostic indicators and guess work to determine whether or not a laparoscopic cystectomy can be safely attempted. This uncertainty and the fear of spillage cause many physicians not to attempt laparoscopic ovarian cystectomy or to feel very uncomfortable doing it.

Thus, a need exists for methods and apparatuses for performing a laparoscopic ovarian cystectomy safely and easily, without spilling the contents of the cyst into the peritoneal cavity. This will reduce the number of patients who suffer the harmful consequences of cyst spillage. This will also allow more laparoscopic ovarian cystectomies, instead of laparotomies or oophorectomies, to be performed.

The prior art discloses several types of endo-bags for use during a laparoscopic procedure. U.S. Pat. No. 5,215,521 to Cochran et al. discloses an entrapment envelope which is inserted through a laparoscopic port for removal of a surgically severed organ.

U.S. Pat. No. 6,059,793 to Pagedas discloses a reusable bag for retrieval of a mass, such as an excised organ, through a laparoscopic sleeve and also allows for morsellizing the severed organ.

U.S. Pat. No. 6,270,505 to Yoshida et al. discloses an inflatable endo-bag for organ removal, ports for surgical instruments and a closing string.

All of the prior art references discussed above are drawn to encapsulation of an organ after it has been surgically severed from its attachments to the body. In particular, all of these prior art references address the problem of transport of an organ outside the abdominal cavity after it has been laparoscopically excised inside the abdominal cavity. Accordingly, these prior art references do not address the special problem of separating a mass, such as a cyst, from a live, intact organ such as an ovary without rupture of the cyst and spillage of its contents.

U.S. Pat. No. 5,279,539 to Bohan et al. discloses a bioabsorbable surgical pouch which can be placed over an ovary after a surgical procedure to prevent surgical adhesions. However, Bohan et al. do not disclose the use of the pouch during a surgical procedure such as performing an ovarian cystectomy.

There are typically two steps involved in the removal of an ovarian cyst by laparoscopy. The first step is the separation of the cyst from the ovary. The second step is the transport of the cyst outside of the abdominal cavity once it has been separated from the ovary. There are problems associated with each step. The problem in the first step is how to separate the cyst from the ovary without rupturing the cyst and spilling its contents. The problem with the second step is how to transport a large cyst outside the abdominal cavity through a small opening in the abdomen. All of the prior art discussed above are involved only with the problem associated with the second step, that is, transport of a mass or organ outside the abdomen after it has been excised.

SUMMARY OF THE INVENTION

Preferred embodiments of the present invention address the first problem, specifically, separation of a mass such as a cyst from an ovary without spilling its contents into the abdominal cavity. It will be appreciated, however, that the methods and apparatuses discussed herein are not limited to ovarian cystectomies, and therefore, may have applicability to any procedure wherein it is desired to remove biological or other material from an organ, or to remove an organ itself, in a contained environment.

Several unique features are disclosed by the preferred embodiments discussed below. First, in one embodiment, an intact organ is encapsulated, preferably with a non-permeable bag-type structure, while it is still attached to the body. As used herein, an intact organ is defined as an organ that is still attached to the body as found in its natural state. The intact organ is preferably a live intact organ. However, intact organs which contain dead tissue are also encompassed within the present invention. The encapsulation of an intact organ is in contrast to the prior art references discussed above, wherein encapsulation can only occur after the organ or mass has been completely separated from its attachment to the body. Thus, in the prior art discussed above, the organ or mass is first completely excised and then encapsulated. In preferred embodiments of the present invention, the organ or mass is first encapsulated and then the process of excision is performed. These embodiments advantageously allow a mass, such as an ovarian cyst, for example, to be separated from the ovary without spilling its contents into the abdominal cavity.

In one embodiment, the disclosed bag surrounding the intact organ is provide with multiple openings for insertion of one or more instruments. These instruments may be inserted simultaneously to perform operations on an intact organ such as removal of a cyst from an ovary, or other desired procedures. In one embodiment, openings are provided with a one-way valve.

In one embodiment, the bag is a balloon-like structure designed to prevent spillage of the cyst content into the peritoneal cavity and thus make laparoscopic ovarian cystectomy safe and easy. The balloon-like structure preferably comprises an inflatable, water-tight, fire-retardant bag with an opening on a distal side thereof and a gas nozzle on a proximal side hereof. In a preferred embodiment, the bag is funnel-shaped and has a large noose-like opening at the distal end. In one embodiment, the proximal end is long and tapered. In a preferred embodiment, the distal end has a relatively large opening, at least large enough to encapsulate an ovary or other organ.

The bag in one embodiment used for laparoscopic ovarian cystectomy is introduced into the peritoneal cavity through a laparoscopic port, the proximal end with the gas nozzle being retained on the outside of the body for gas infusion. Once inside the peritoneal cavity, the large distal opening of the bag is then placed over the ovary and fastened. In a preferred embodiment, a noose is tightened down over the ovarian pedicle and locked in using a fastening device such as a trumpet valve. As used herein, the term "pedicle" is used in its ordinary sense and refers to any stem-like structure that extends from an organ. The term "ovarian pedicle" is used in its ordinary sense and should be interpreted to include a combination of the infundibulo-pelvic ligament, the utero-ovarian ligament and/or the meso-ovarian ligament. In the presence of an ovarian cyst, these tissues can become elongated to form a slender stem-like structure that is herein referred to as the ovarian pedicle. Tightening the noose around this ovarian pedicle allows the bag to completely envelop the ovary and its cyst and form an air-tight seal. In a preferred embodiment, gas is then infused through the gas nozzle to inflate the bag.

In a preferred embodiment, a laparoscopic camera and other instruments can now passed into the inflated bag through one-way valves to operate on the cyst. Any leakage of cyst content during the surgery is now contained within the bag and therefore does not come into contact with the peritoneal cavity and its organs. In a preferred embodiment, the cyst can be deflated without any concern for contamination and the cystectomy performed much easier and faster on a collapsed cyst. An additional advantage of the bag is that it also prevents accidental and harmful contact between the laparoscopic instruments and other organs such as the bowel or bladder.

After the cystectomy is completed, any fluid leakage into the bag is removed by laparoscopic suction and the bag thoroughly irrigated. The noose is then loosened and the ovary removed from the bag. The noose is closed again and the bag, containing the specimen, is removed from the peritoneal cavity through a laparoscopic port.

The preferred methods and apparatuses described above and in further detail below allow for a safe, rapid and easy laparoscopic ovarian cystectomy because it circumvents the most difficult and time-consuming aspect of the surgery, i.e., the prevention of cyst spillage into the peritoneal cavity.

For purposes of summarizing the invention and the advantages achieved over the prior art, certain objects and advantages of the invention have been described above. Of course, it is to be understood that not necessarily all such objects or advantages may be achieved in accordance with any particular embodiment of the invention. Thus, for example, those skilled in the art may recognize that the invention may be embodied or carried out in a different manner that achieves or optimizes one advantage or group of advantages as taught herein without necessarily achieving other objects or advantages as may be taught or suggested herein.

Accordingly, in one embodiment, a surgical device is disclosed for enclosing an intact organ to perform a surgical procedure thereon. The device includes a non-permeable material adapted to be closed over an intact organ while substantially enclosing the intact organ and at least one port in the non-permeable material adapted to allow a surgical instrument to pass therethrough to operate on the intact organ. In a preferred embodiment, the non-permeable material is an inflatable bag and preferably includes a nozzle at one end for inflating the bag while the material is closed over the intact organ.

In a preferred embodiment, the intact organ is an ovary.

In one embodiment, a surgical device for enclosing an intact organ to perform a surgical procedure thereon is disclosed which includes an inflatable bag comprising flexible material and having an opening at a distal end thereof sufficiently large to receive the intact organ and a nozzle at a proximal end thereof adapted to inflate the bag and at least one port which includes a one-way valve to allow a surgical instrument to be introduced into the bag to perform a surgical operation on the intact organ contained within the bag without leakage of gas. In a preferred embodiment, the intact organ is an ovary.

In a preferred embodiment the surgical device includes an insertion housing for enclosing the bag. In a preferred embodiment, the surgical device also includes a plurality of ports to allow surgical instruments to be introduced into the bag.

In another embodiment a method of performing a cystectomy is disclosed which includes the steps of: (1) introducing an inflatable bag into an abdominal cavity of a patient, wherein a distal end of the inflatable bag has an opening sufficiently large to encapsulate an ovary which is attached to the body; (2) positioning the inflatable bag over the ovary to encapsulate the ovary; (3) closing the opening of the inflatable bag over an ovarian pedicle; (4) inflating the bag; and (5) introducing one or more instruments into the bag to separate a cyst from the encapsulated ovary.

In a preferred embodiment, the method includes inserting the bag into the abdominal cavity within an insertion housing.

In another embodiment, a method of performing an operation on an intact organ, is disclosed which includes the steps of: (1) introducing a non-permeable structure into a body space near to the intact organ; (2) enclosing at least a portion of the intact organ with the non-permeable structure, the non-permeable structure defining a working space between the intact organ and the non-permeable structure; and (3) introducing one or more instruments through the non-permeable structure to perform the operation on the intact organ within the working space.

Further aspects, features and advantages of this invention will become apparent from the detailed description of the preferred embodiments which follow.

BRIEF DESCRIPTION OF THE DRAWINGS

These and other feature of this invention will now be described with reference to the drawings of preferred embodiments which are intended to illustrate and not to limit the invention.

DETAILED DESCRIPTION OF THE PREFERRED EMBODIMENTS

While the described embodiments represent preferred embodiments of the present invention, it is to be understood that modifications will occur to those skilled in the art without departing from the spirit of the invention. The scope of the invention is therefore to be determined solely by the appended claims.

Briefly stated, preferred embodiments relate to a bag used to encapsulate an ovary for performing a cystectomy, and methods for delivering the bag and for performing the cystectomy. It will be appreciated, however, that the methods and apparatuses taught herein are not limited to ovarian cystectomies, and thus, other procedures may benefit from the embodiments described herein.

Figure 1A:
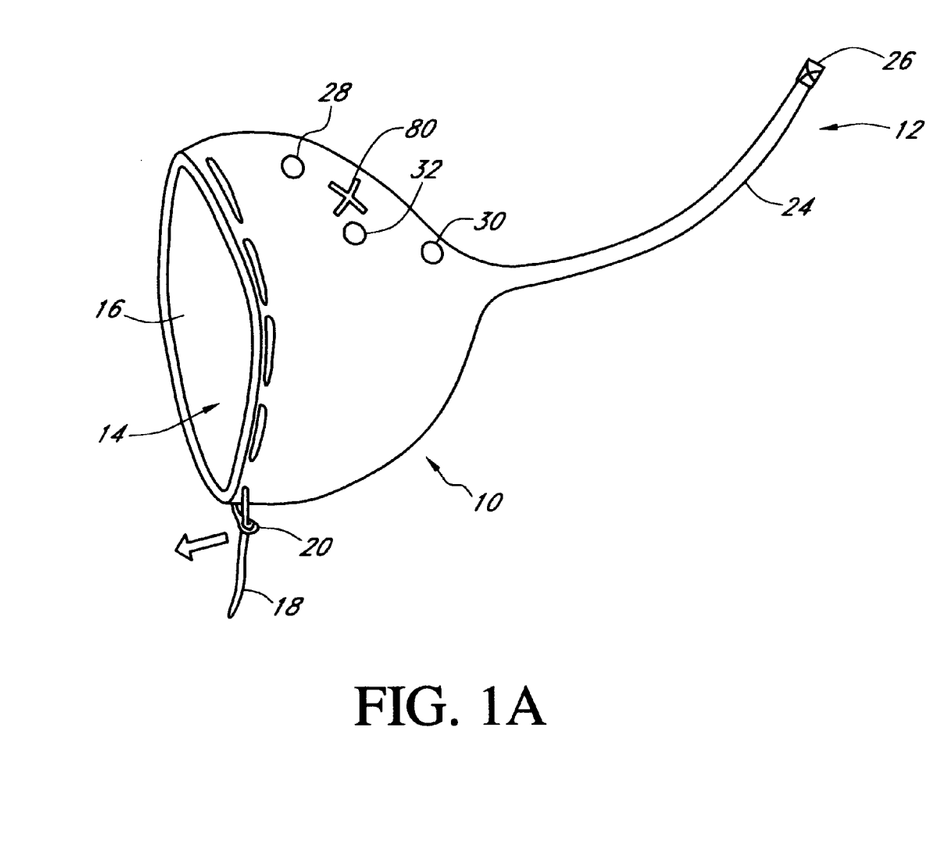
FIG. 1A is a perspective view of a bag according to one embodiment of the present invention.

FIG. 1A shows one embodiment of a bag 10 to be used to perform the cystectomy. The bag as illustrated is generally funnel-shaped and has a proximal end 12 and a distal end 14. At the distal end 14, an opening 16 is provided which is sized and configured to fit over an organ such as an ovary. As illustrated, the opening 16 can be circular, or may have any other shape as desired that is adapted to form a substantially air tight seal with a portion of an organ such as an ovarian pedicle. In one embodiment, a drawstring 18 is provided near the edge of the opening 16, and is adapted to be pulled taut over a tissue pedicle to seal and lock the bag. The drawstring 18 may be made of any stretchable, rubberband-like material or non-stretchable material including but not limited to an elastic band, rubber band, suture material, etc., or any other desired material.

Figure 1B:
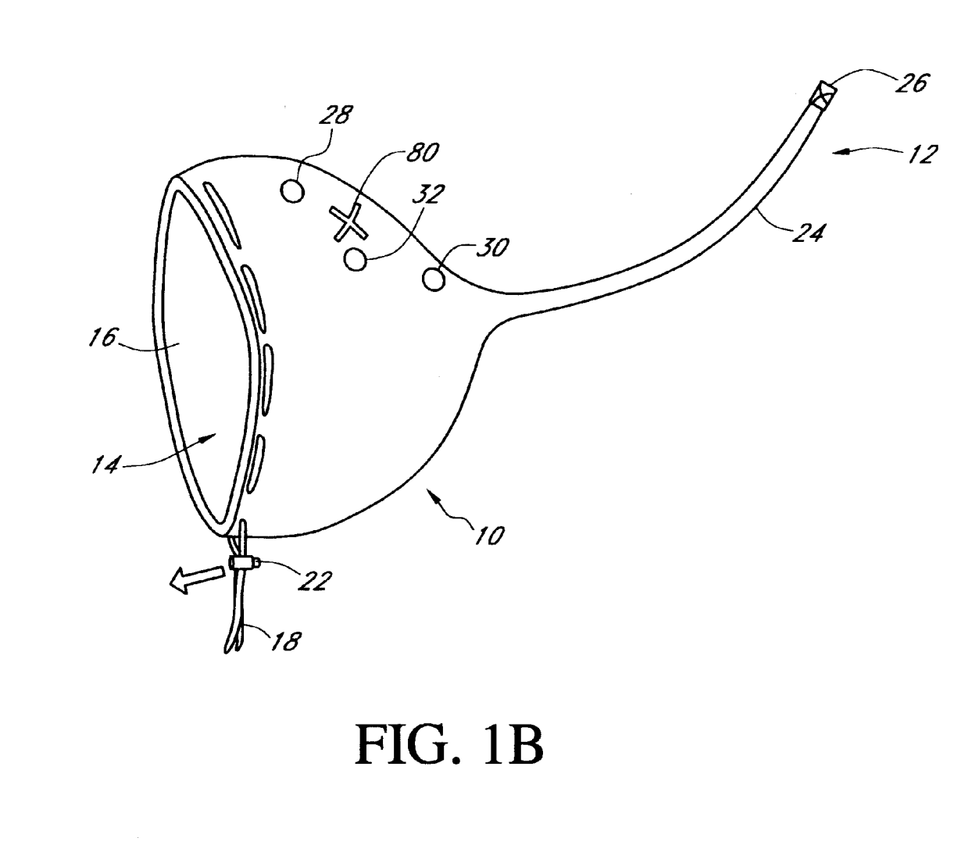
FIG. 1B is a perspective view of a bag having a trumpet valve according to another embodiment of the present invention.

In the embodiment illustrated in FIG. 1A, to close the bag over a pedicle, the drawstring 18 is pulled through a noose 20 to seal and lock the bag. Other embodiments may also be used to seal and lock the bag, such as a noose over a button, a velcro fastening or a pre-tied suture. FIG. 1B illustrates one embodiment wherein the drawstring 18 can be closed using a trumpet valve 22. It will be appreciated that other means may be used to seal the bag 10. In one embodiment, closure of the opening 16 of the bag 10 over a tissue pedicle may be further reinforced with a separate rubber band placed around the outside of the bag near the opening 16.

The bag itself may be made of any flexible material that is capable of being blown up like a balloon including, but not limited to, plastic material, latex, or rubber. The balloon material may be compliant in order to fill the desired space within the patient, or may be non-compliant to inflate to a predetermined size. It will be appreciated, however, that the invention is not to be limited to inflatable structures. Any non-permeable structure capable of isolating an organ to be treated from surrounding organs or bodily space will be suitable in performing the cystectomy or other procedure. For example, expandable structures (both self-expanding and non-self-expanding) may be used.

At the proximal end 12 of the bag 10, away from the opening 16, the bag preferably tapers into a long tube 24. At or near the very proximal end of the tube 24, a gas nozzle 26 may be provided to allow for inflation of the bag. The tube 24 and the gas nozzle 26 are preferably adapted to extend outside of the body and allows for infusion of gas to blow up the bag 10 when the opening is sealed over a tissue pedicle. The gas nozzle 26 preferably includes a one-way valve to allow gas or other fluid to be delivered into the bag and maintain inflation of the bag.

As illustrated in FIG. 1A, the bag may also have additional openings or ports 28, 30, and 32 (see also FIGS. 3–9) to allow for insertion of surgical instruments, as described below. These ports 28, 30, and 32 may be placed at desired locations on the outside of the bag to allow for the insertion of appropriate surgical instruments at desired locations. Preferably, each of these ports includes a one-way valve, as described below, to prevent gas inside the bag from escaping when an instrument is inserted therethrough.

Figure 2:
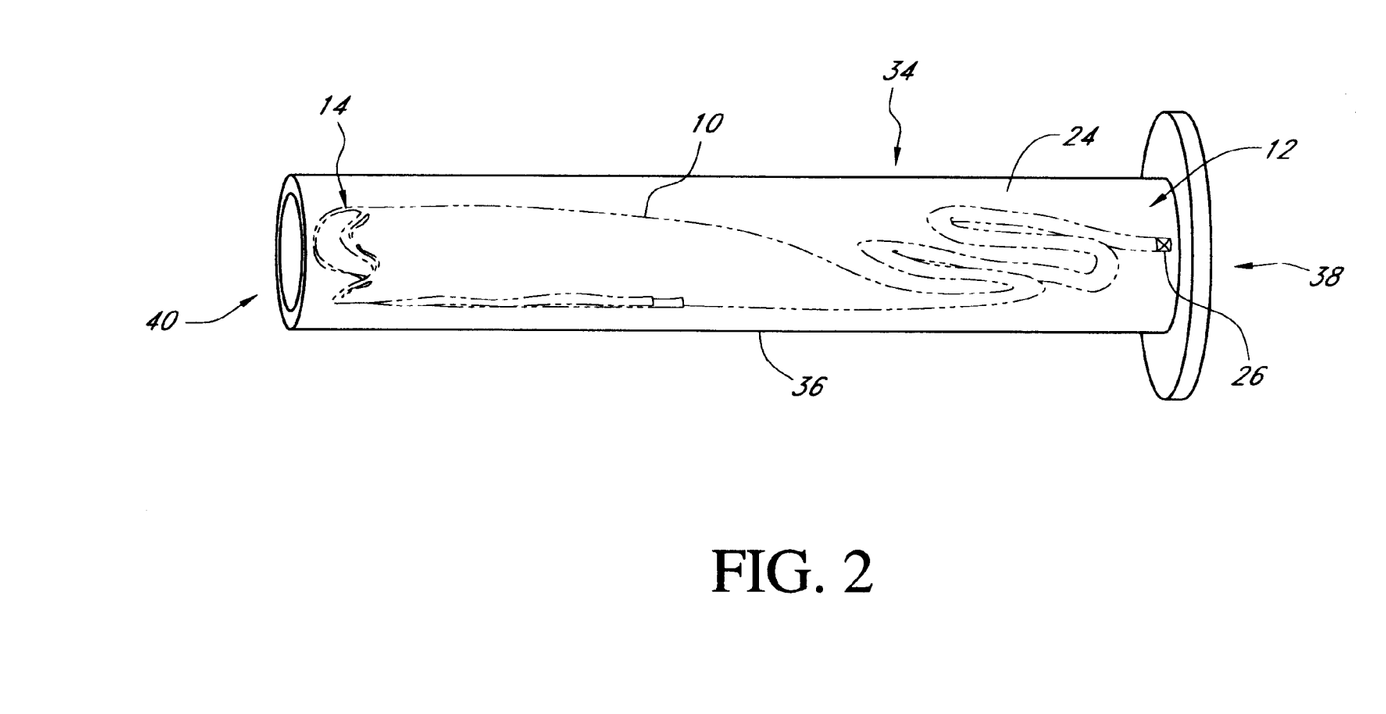
FIG. 2 is a side view of an insertion housing for inserting the bag of FIG. 1A or 1B, with the bag shown inside the insertion housing in phantom.

FIG. 2 illustrates an insertion housing 34 used in one embodiment to insert the bag 10 into a patient. The insertion housing preferably includes a tubular body 36 having a proximal end 38 corresponding to the proximal end 12 of the bag 10, and a distal end 40 corresponding to the distal end 14 of the bag 10. The insertion housing may be made of any relatively hard, biologically non-reactive material including but not limited to plastic materials. FIG. 2 illustrates the bag 10 inside the insertion housing 34 before insertion into the body in a compressed configuration. The distal end 40 of the housing is preferably open and the proximal end 38 of the housing is preferably closed prior to delivery of the bag 10. Further details regarding delivery of the bag into a patient using the insertion housing 34 are described below.

Figure 3:
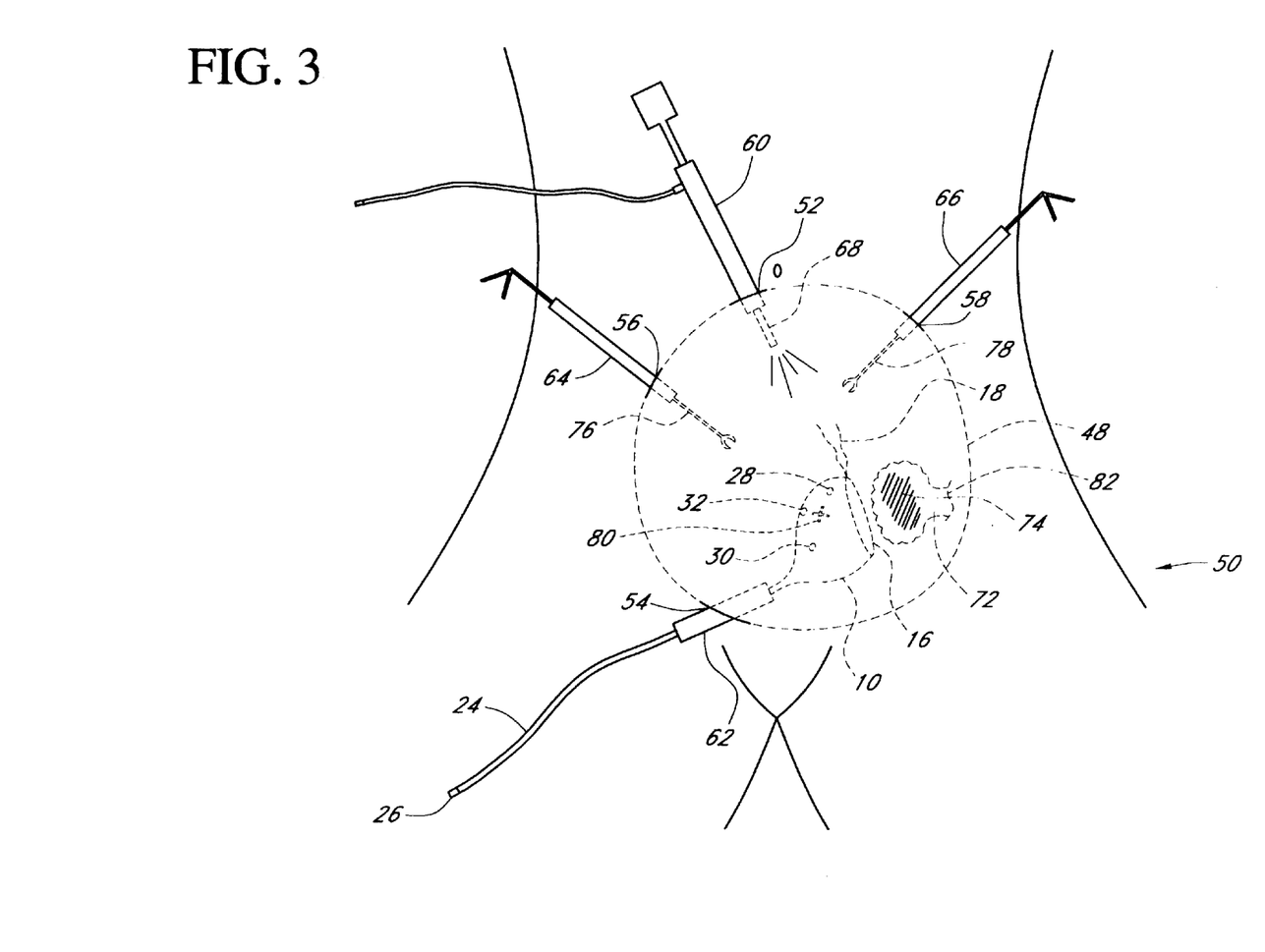
FIG. 3 is a schematic view of the bag of FIG. 1A after insertion into the abdomen via the suprapubic port under visualization by a laparoscopic camera.

FIG. 3 illustrates one embodiment for inserting the bag 10 into the peritoneal or abdominal cavity 48 of a patient 50. As illustrated, a plurality of incisions ranging from 5–10 mm 52, 54, 56, 58 are made in the patient 50. Then, using standard laparoscopic techniques, trocars and trocar sleeves are inserted into the abdomen. After the trocars are removed, the trocar sleeves 60, 62, 64 and 66, as described further below, remain extending from the outside of the patient. The trocar sleeves 60, 62, 64 and 66 each preferably includes a one-way valve such that when instruments are passed through the trocar sleeves into the abdomen of the patient, gas from inside the abdomen, as described below, does not escape. The trocar sleeves described in the embodiments herein preferably have a size of 5 mm or 10 mm. However, it will be appreciated that any size trocar sleeve may be used that is appropriate to carry out the surgical procedure. Different ports and adapters may also be used as needed.

In the embodiment illustrated in FIG. 3, the laparoscope 68 is preferably inserted into the abdomen through a trocar sleeve 60 near the navel. Gas, preferably carbon dioxide, is introduced into the abdominal cavity via one of the trocar sleeves, such as sleeve 60. The intra-abdominal pressure is preferably maintained at a constant level using well-known methods and apparatus.

The bag 10 is preferably introduced into the abdominal cavity 48 through a second 5 or 10 mm trocar sleeve 62 via a suprapubic incision 54 or any other location as desired by the surgeon. In one embodiment, the insertion housing holding the bag, described above, is inserted through the trocar sleeve 62 until its distal end 14 (corresponding to the opening of the bag 16) enters the abdominal cavity as shown in FIG. 3. In a preferred embodiment, the outer diameter of the housing is a perfect fit with the inner diameter of the trocar sleeve 62 such that when the housing is passed through the trocar sleeve, $CO_2$ gas from within the abdomen is prevented from escaping due to the housing 34 being sealed at its proximal end 38.

After the housing is delivered through the trocar sleeve 62 into the abdomen, the bag is then grasped from the distal end of the insertion housing with a laparoscopic grasper 78 while the insertion housing 34 is pulled out, leaving the gas nozzle 26 on the outside of the body. Preferably, the gas nozzle 26 will be of such size and material such that it will form a tight seal with the one-way valve of the trocar sleeve 62. A 10–5 mm seal reducer may be used if necessary to achieve a tight seal. It will be appreciated that other methods and apparatuses may be used to insert the bag 10 into the abdomen 48 of a patient 50.

Figure 4:
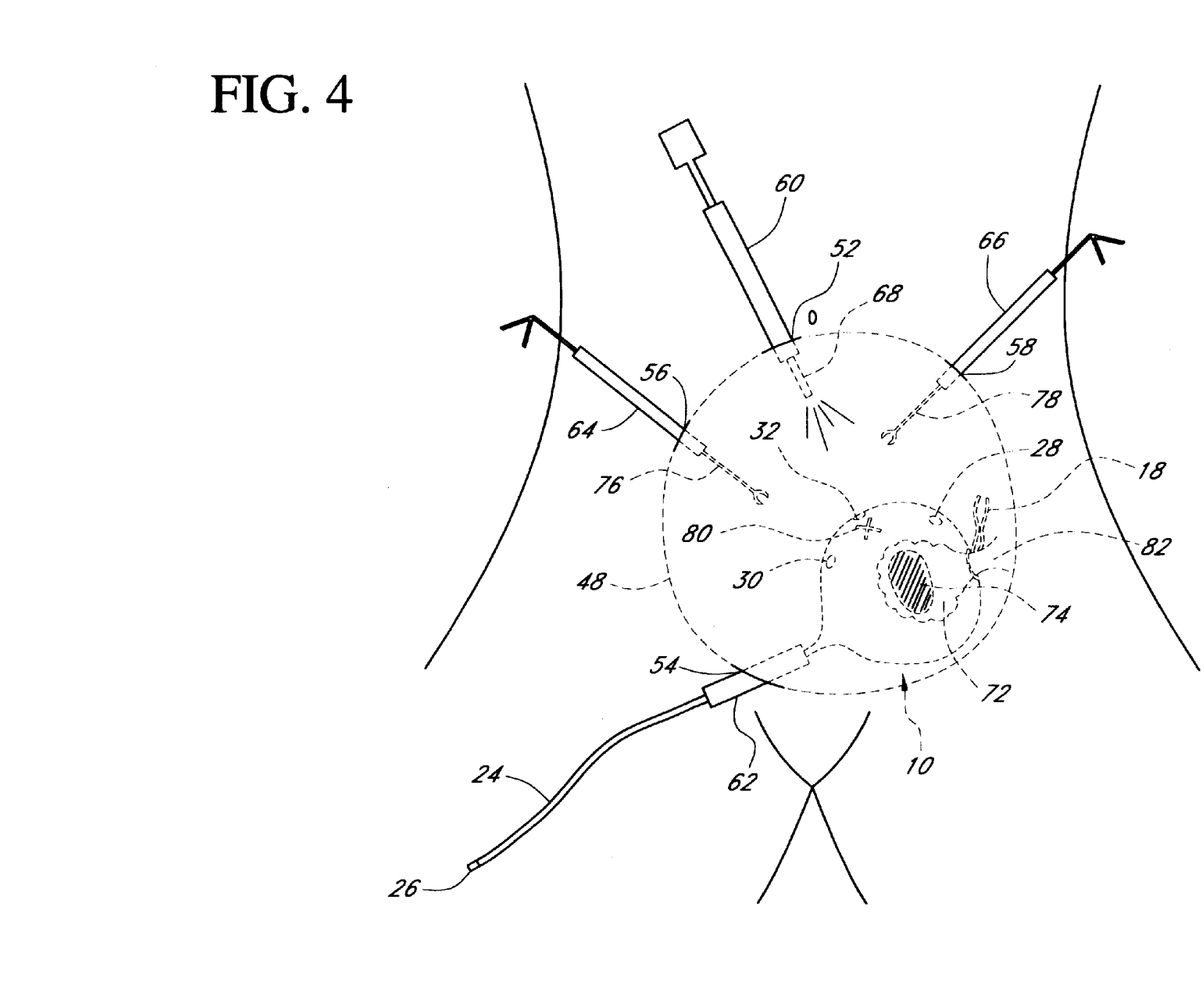
FIG. 4 is a schematic view of the bag of FIG. 3 after placement around an ovary and cyst and after a noose on the bag has been tightened down.

As shown in FIG. 4, in performing an ovarian cystectomy, once inside the abdominal cavity the bag 10 is preferably maneuvered such that the opening 16 of the bag 10 is placed over the ovary 72 having a cyst 74 and the ovarian pedicle 82. Positioning of the bag is facilitated by the use of laparoscopic instruments 76 and 78 that can be inserted into the abdomen. In one embodiment, ports 28, 30, and 32 containing one-way valves on the bag 10 are generally lined up, respectively, with the trocar sleeves 66, 64, and 60, extending into the patient's abdomen, so that the laparoscope 68 and other laparoscopic instruments 76, 78 passing through these sleeves can be directly inserted into these ports 28, 30, and 32. The bag 10 may also have one or more external markings 80 to help guide the alignment of the ports on the bag 28, 30, 32 with the trocar sleeves 66, 64, and 60. As shown in FIG. 4, a mark 80 on the bag 10 may be used to align the port 32 with the trocar sleeve 60 and the laparoscope 68.

Once the opening 16 is positioned over the ovary 72 and the ovarian pedicle 82 and the bag is properly aligned, the opening is closed over the ovarian pedicle as shown in FIG. 4. Closure can occur using a noose 20 or other methods as described with respect to FIGS. 1A and 1B above. Laparoscopic instruments such as grasping forceps 76, 78 may be used to assist in closing the bag 10.

Gas, preferably carbon dioxide, is then infused into the bag 10 via the gas nozzle 26 to inflate the bag. The bag 10 may be inflated as required to provide a space to perform the surgery and in one embodiment, may be inflated up against the abdominal wall 48.

With the bag inflated, the ports 28, 30 and 32 on the bag are preferably aligned with the incisions 58, 56 and 52 and the trocar sleeves 66, 64 and 60, respectively. If the bag is not properly aligned upon initial inflation, the physician can use grasping instruments such as grasping forceps 76, 78 which are inserted into the abdominal cavity 48 but have been inserted into the bag to finalize the alignment of the bag.

Figure 5:
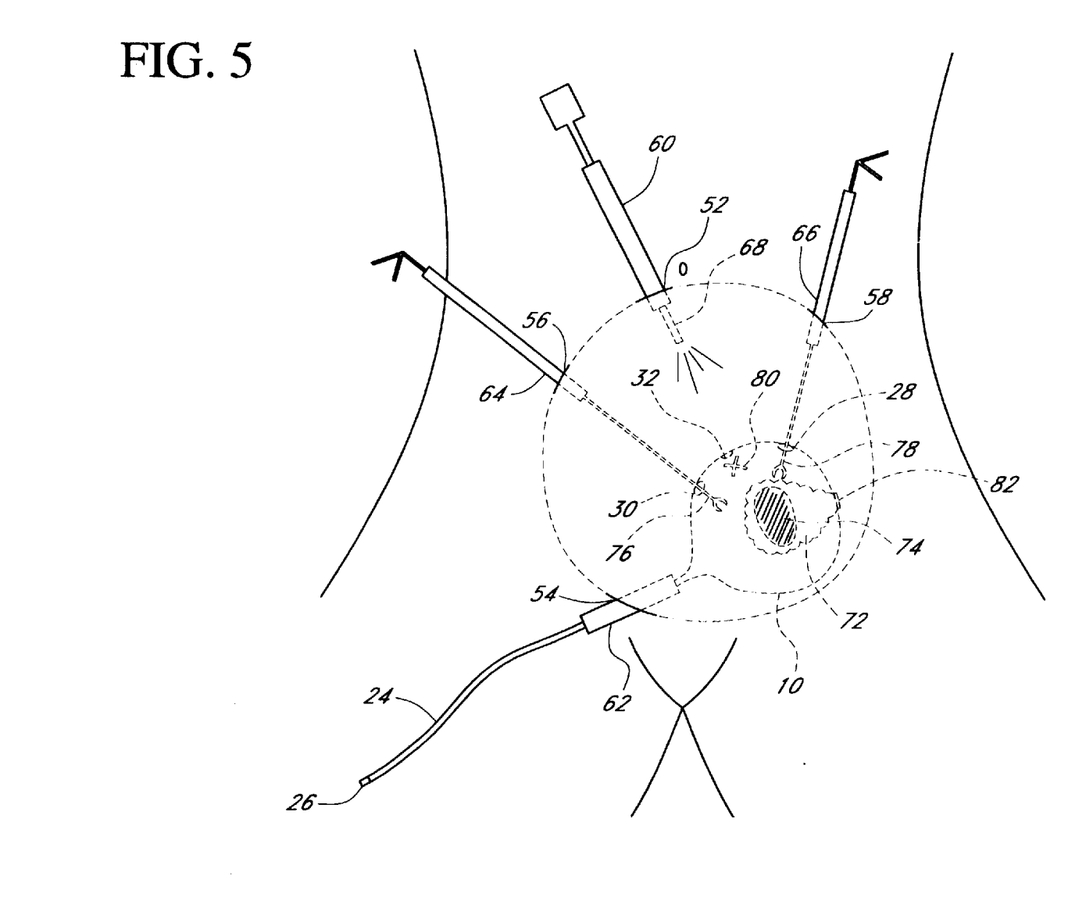
FIG. 5 is a schematic view of instruments inserted into the inflated bad through one-way valves under guidance by the laparoscopic camera.

FIG. 5 illustrates the bag after it has been inflated in the abdominal cavity 48 with instruments inserted into the bag 10. The laparoscope remains outside of the bag 10, but inside the abdominal space to allow the operator to visualize where the instruments will be inserted through the bag. Instruments, including but not limited to grasping forceps, blunt probes, needle electrodes or laparoscopic scissors, etc. may be inserted into the ports 28 and 30 on the bag 10. Each of these ports 28 and 30 preferably includes a one-way valve to allow for insertions of the instruments without leakage of gas.

Figure 6A:
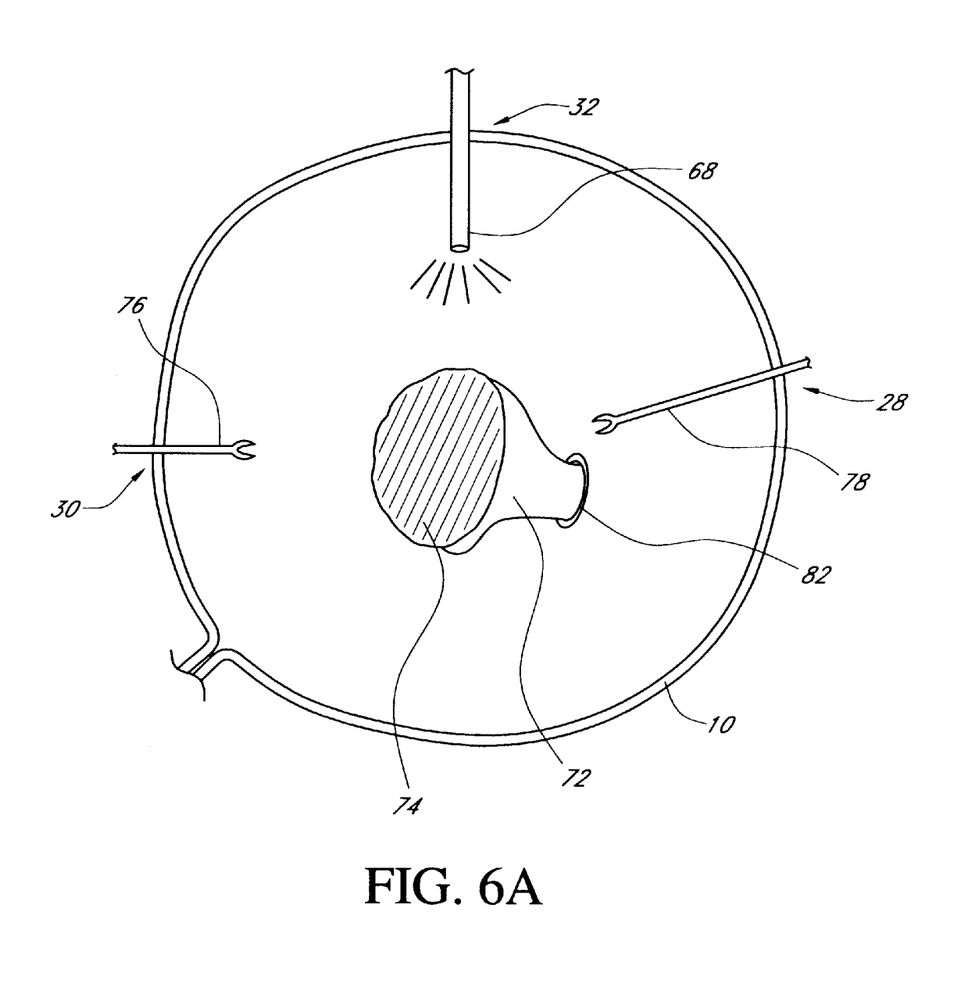
FIG. 6A is a schematic view of the inflated bag within the abdominal cavity, showing the laparoscopic instruments and camera inside the bag, ready to operate on the cyst.
Figure 6B:
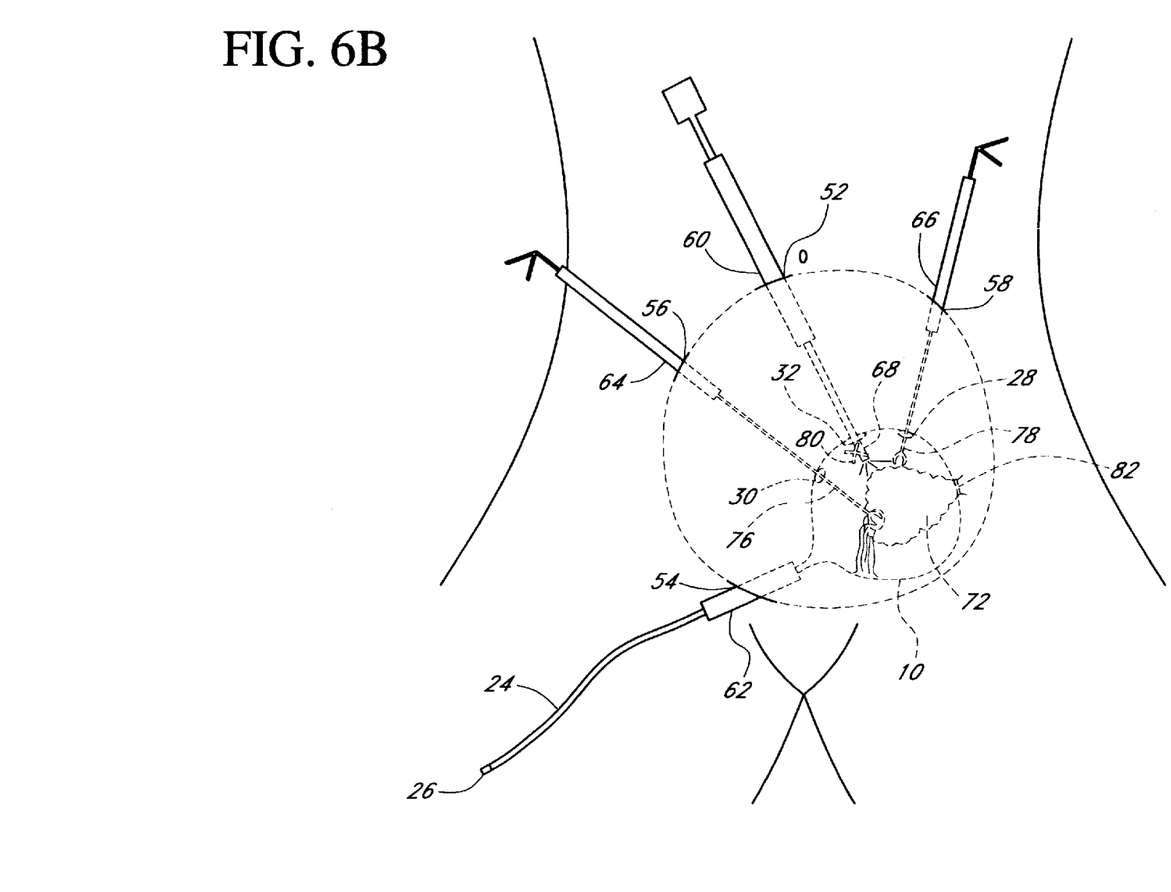
FIG. 6B is a schematic view showing surgery inside the bag, in this case, puncturing and decompressing the cyst.

As shown in FIGS. 6A and 6B, after the instruments 76 and 78 are inserted into the bag 10, the laparoscope 68 is then inserted through a port 32 in the bag 10 to provide visualization for the procedure inside the bag 10. The cystectomy or other procedure is then performed under direct visualization by methods well known to those skilled in the art. More instruments may be inserted into the bag to help facilitate the procedure if so desired by the surgeon.

In one preferred embodiment, after the laparoscope 68 and instruments 76 and 78 are inserted into the bag 10, the cyst 74 can safely be punctured and deflated before excision using one of the instruments (FIG. 6B). This is in contrast to procedures performed in the past, where physicians would use great care not to puncture the cyst to avoid leakage into the peritoneal cavity. In this embodiment of the invention, any leakage of fluid is advantageously contained within the bag. This allows the cystectomy to be safely and easily performed by the laparoscopic method, regardless of the nature of the cyst. In fact, no matter what type of cyst is present, with the preferred embodiments of the invention described above, there is no leakage of fluid into the peritoneal, cavity. Consequently, even an inexperienced surgeon can perform a laparoscopic ovarian cystectomy using the bag described above because any fluid leakage from a malignant, dermoid or mucinous cyst is retained safely within the bag. Another advantage with a preferred embodiment of the invention is that because of the ability to deflate the cyst safely, even a very large cyst which formerly would have required a laparotomy even by an experienced surgeon, can now be easily removed by laparoscopy.

Figure 7:
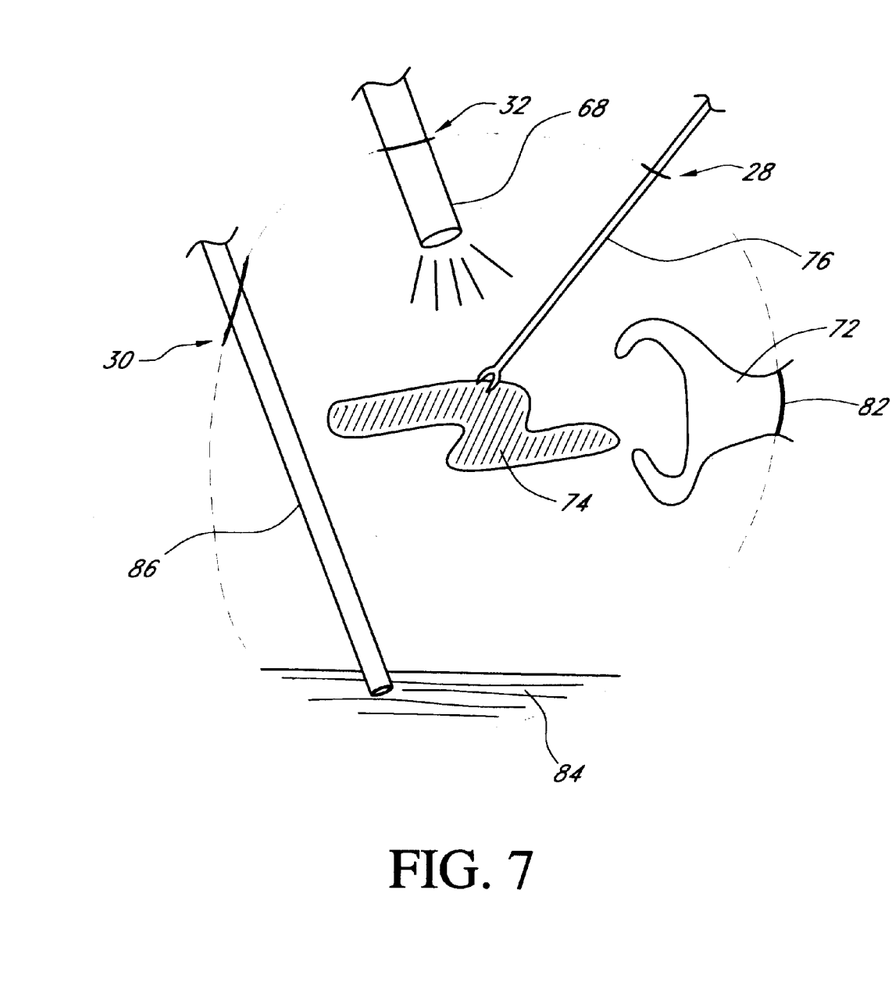
FIG. 7 is a schematic view of the interior of the bag after the cyst has been separated from the ovary and the spilled cyst content is being removed from the bag via laparoscopic suction.

Once the cyst is punctured and the fluid has leaked out, the cyst 74 often becomes easier to remove from the ovary 72. As shown in FIG. 7, the punctured cyst 74 can be removed and separated from the ovary using known techniques. Alternatively, should the surgeon prefer, the cystectomy can proceed without first deflating the cyst. However any accidental cyst leakage during the procedure would still be contained within the bag 10. In a preferred embodiment, any spillage 84 caused by the procedure is removed with a laparoscopic suction-irrigator 86 and the bag is thoroughly cleansed with irrigation. In one embodiment, a suction-irrigator 86 is inserted through one of the ports 30 in the bag 10 to irrigate and remove any loose substances or fluid. After irrigation and suction of the fluid in the bag, the instruments 76, 86 and laparoscope 68 may be removed through the ports 28, 30, and 32.

Figure 8:
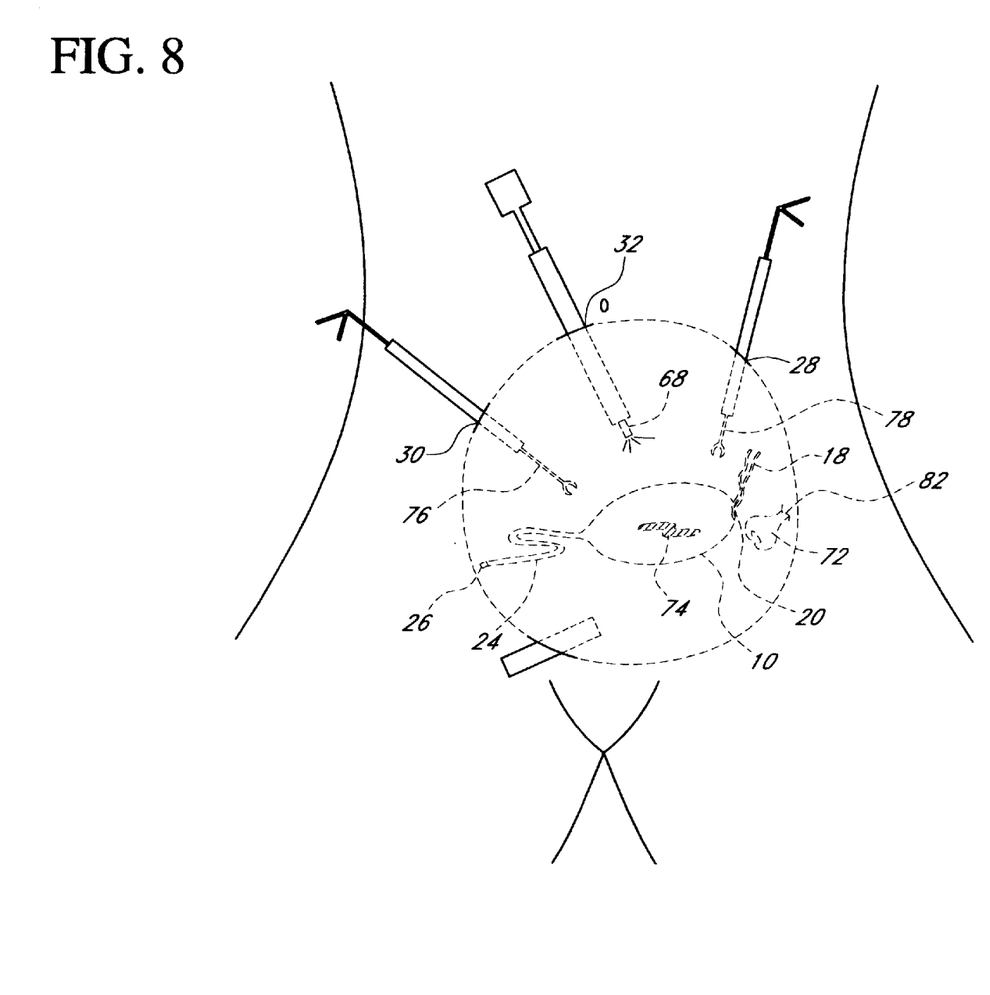
FIG. 8 is a schematic view of the bag after deflation, wherein the instruments and the ovary are removed from the bag, the noose is tightened down to close the bag and the gas nozzle is inserted into the abdomen.

As shown in FIG. 8, after irrigation, suction, and instrument removal, the bag is deflated while the noose over the ovarian pedicle 82 is loosened to allow removal of the ovary 72 from the bag 10. The noose 20 can then be tightened again using the surgical instruments 76, 78 which are now outside the bag but still within the abdominal space to seal off the bag 10 with the excised cyst 74 inside as shown in FIG. 8. In a preferred embodiment, as described above, the cyst 74 has been punctured and deflated. Consequently, it is now much smaller and the bag 10 containing it may be easily removed through one of the trocar sleeves. However, in some embodiments where the tissue mass is still large, it may be desirable to reduce the size of the tissue prior to deflating the bag by grinding the tissue with an instrument designed for that purpose such as a morsellizer (see U.S. Pat. No. 6,059,793 to Pagedas which is incorporated herein by reference).

Figure 9:
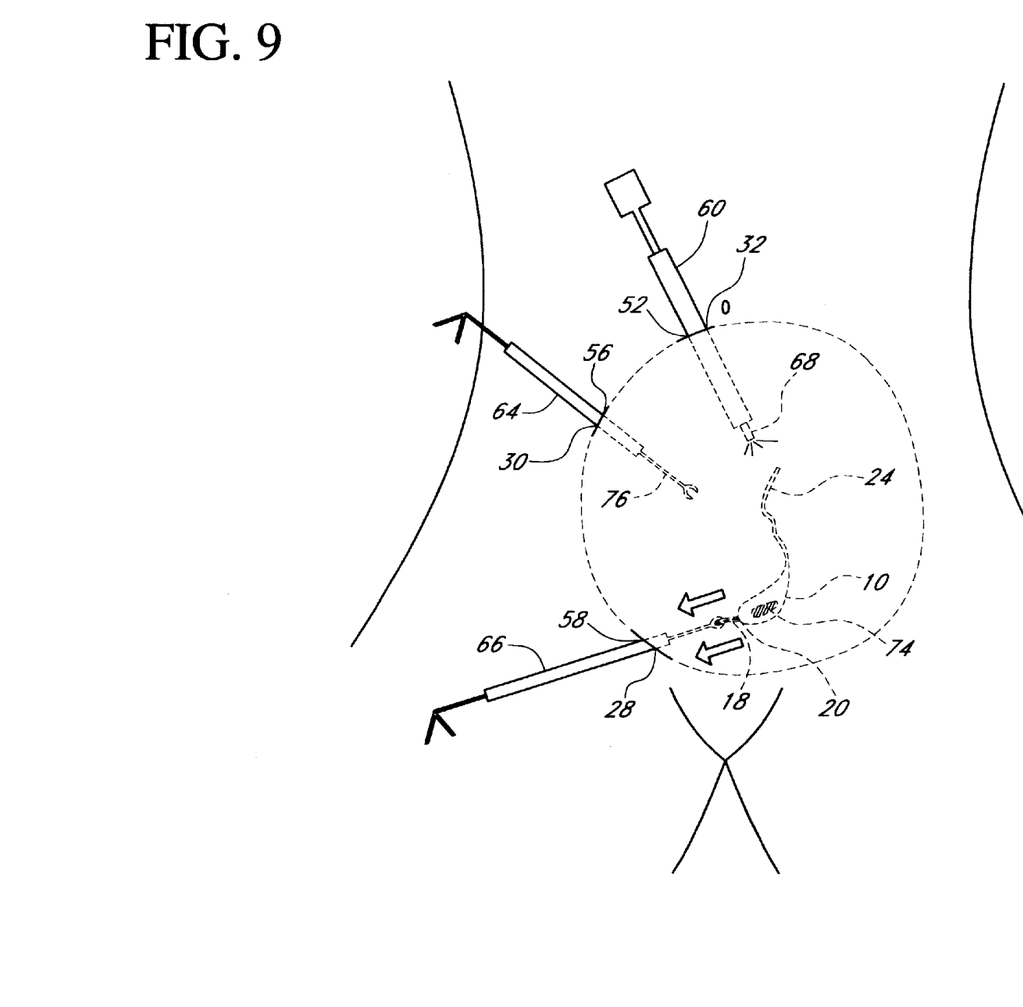
FIG. 9 is a schematic view of the deflated bag containing the cyst as it is removed from the abdomen through a laparoscopic port.

The bag is desirably removed through one of the trocar sleeves inserted through one of the laparoscopic incisions. In one embodiment, the tube 24 and the gas nozzle 26 of the bag 10 are pushed into the abdomen as shown in FIG. 8. FIG. 9 shows removal of the deflated bag 10 containing the cyst 74 through the trocar sleeve 66. It will be appreciated that the bag can be removed through any of the trocar sleeves. In a preferred embodiment, the bag is grabbed by the tightened noose 20 and the bag 10 with cyst 74 can be easily removed without contamination of the peritoneal cavity.

Preferred embodiments of the present invention allow for excision of a mass such as a cyst after the organ containing the mass, such as an ovary, has been encapsulated in the bag described above. The disclosed bag will allow surgical operation on the ovary without spilling the contents of the cyst into the peritoneal cavity. Consequently, there is a greatly reduced risk of peritonitis from spillage of a dermoid or mucinous cyst and also a greatly reduced risk of contamination of the peritoneal cavity with cancer cells if the cyst turns out to be malignant. Thus, a laparoscopic cystectomy can be performed regardless of the nature and the size of the cyst which is a big advantage for the patient in terms of shorter recovery time, fewer complications and fewer unnecessary oophorectomies and laparotomies. Of course, if the cyst turns out to be malignant, then additional surgery will be necessary. But if it isn't, then the patient would have benefited greatly from the laparoscopic approach. The bag also prevents inadvertent injury to the surrounding structures such as the bowels or the bladder and since the cyst is already deflated during the procedure, the transport of the cyst outside the abdominal cavity is also simplified for the physician.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A surgical device for enclosing an intact organ to perform a surgical procedure thereon, the device comprising:
    a non-permeable material adapted to be closed over an intact organ while substantially enclosing the intact organ; and
    at least one port in the non-permeable material adapted to allow a surgical instrument to pass therethrough to operate on the intact organ.

2. The surgical device of claim 1, wherein the non-permeable material is an inflatable bag.

3. The surgical device of claim 2, wherein the bag is substantially funnel-shaped.

4. The surgical device of claim 2, wherein the bag includes a nozzle at one end for inflating the bag while the material is closed over the intact organ.

5. The surgical device of claim 1, wherein the intact organ is a live intact organ.

6. The surgical device of claim 1, wherein the intact organ is an ovary.

7. The surgical device of claim 1, wherein the non-permeable material is adapted to be closed over a pedicle of the intact organ.

8. A surgical device for enclosing an intact organ to perform a surgical procedure thereon, comprising:
    an inflatable bag comprising flexible material and having an opening at a distal end thereof sufficiently large to receive the intact organ and a nozzle at a proximal end thereof adapted to inflate the bag; and
    at least one port comprising a one-way valve to allow a surgical instrument to be introduced into the bag to perform a surgical operation on the intact organ contained within the bag without leakage of gas.

9. The surgical device of claim 8, wherein the intact organ is a live intact organ.

10. The surgical device of claim 8, wherein the intact organ is an ovary.

11. The surgical device of claim 8, further comprising a drawstring near the opening to close the opening.

12. The surgical device of claim 8, wherein the opening at the distal end comprises a noose-like opening.

13. The surgical device of claim 8, further comprising an insertion housing for enclosing the bag.

14. The surgical device of claim 8, comprising a plurality of ports to allow surgical instruments to be introduced into the bag.

15. A method of performing a cystectomy, comprising:
    introducing an inflatable bag into an abdominal cavity of a patient, wherein a distal end of the inflatable bag has an opening sufficiently large to encapsulate an ovary which is attached to the body;
    positioning the inflatable bag over the ovary to encapsulate the ovary;
    closing the opening of the inflatable bag over an ovarian pedicle;
    inflating the bag; and
    introducing one or more instruments into the bag to separate a cyst from the encapsulated ovary.

16. The method of claim 15, further comprising removing the bag from the ovarian pedicle and releasing the ovary from the bag.

17. The method of claim 16, further comprising re-closing the opening of the bag with the ovary outside the bag and with the removed cyst inside the bag.

18. The method of claim 17, further comprising transporting the separated cyst outside of the abdominal cavity within the inflatable bag.

19. The method of claim 15, wherein the inflatable bag is inflated through a gas nozzle on the proximal end on the inflatable bag outside of the abdominal cavity.

20. The method of claim 15, wherein introducing the inflatable bag into the abdominal cavity comprises inserting the bag into the abdominal cavity within an insertion housing.

21. The method of claim 15, wherein the bag is sufficiently inflated to allow for the performance of the cystectomy inside the bag.

22. The method of claim 15, further comprising irrigating the inflatable bag after separating the cyst from the ovary.

23. The method of claim 15, wherein closing the opening of the bag over the pedicle comprises pulling a drawstring closed over the ovarian pedicle.

24. The method of claim 15, wherein introducing one or more instruments into the bag comprises inserting said instruments through ports in the surface of the bag.

25. The method of claim 24, wherein the ports include one-way valves to prevent leakage of gas and fluid from the bag.

26. A method of performing an operation on an intact organ, comprising:

introducing a non-permeable structure into a body space near to the intact organ;

enclosing at least a portion of the intact organ with the non-permeable structure, the non-permeable structure defining a working space between the intact organ and the non-permeable structure; and introducing one or more instruments through the non-permeable structure to perform the operation on the intact organ within the working space.

27. The method of claim 26, wherein the non-permeable structure is an inflatable bag having an opening sized and configured to receive the intact organ.

28. The method of claim 27, wherein enclosing at least a portion of the intact organ comprises positioning the bag over the organ through the opening, and closing the opening over a pedicle extending from the organ.

29. The method of claim 28, wherein enclosing at least a portion of the intact organ further comprises inflating the bag through a nozzle extending outside of the body space.

30. The method of claim 26, wherein introducing one or more instruments through the non-permeable structure comprises inserting said instruments through ports in the surface of the non-permeable structure.

31. The method of claim 26, wherein the intact organ is a live intact organ.

* * * * *